United States Patent [19]
Wagner

[11] Patent Number: 6,133,441
[45] Date of Patent: Oct. 17, 2000

[54] PRODUCTION OF A SALT OF CLAVULANIC ACID

[75] Inventor: Helmut Wagner, Kramsach, Austria

[73] Assignee: Biochemie Gesellschaft m.b.H., Austria

[21] Appl. No.: 09/068,241

[22] PCT Filed: Nov. 14, 1996

[86] PCT No.: PCT/EP96/05015

§ 371 Date: May 11, 1998

§ 102(e) Date: May 11, 1998

[87] PCT Pub. No.: WO97/18216

PCT Pub. Date: May 22, 1997

[30] Foreign Application Priority Data

Nov. 15, 1995 [AT] Austria .................................. 1867/95

[51] Int. Cl.⁷ ............................................... C07D 503/08
[52] U.S. Cl. ........................................................ 540/349
[58] Field of Search ............................................. 540/349

[56] References Cited

U.S. PATENT DOCUMENTS

| | | | |
|---|---|---|---|
| 4,110,165 | 8/1978 | Cole et al. | 195/80 |
| 4,144,242 | 3/1979 | Fleming | 540/349 |
| 4,556,559 | 12/1985 | Cole et al. | 424/114 |
| 4,560,552 | 12/1985 | Cole et al. | 424/114 |
| 4,795,824 | 1/1989 | Kippax | 560/204 |
| 5,210,296 | 5/1993 | Cockrem | 562/589 |
| 5,310,898 | 5/1994 | Copar | 540/349 |
| 5,614,199 | 3/1997 | Zmitek et al. | 424/400 |
| 5,679,789 | 10/1997 | Clark et al. | 540/349 |
| 5,726,170 | 3/1998 | Callewaert | 540/349 |
| 5,734,048 | 3/1998 | Kim | 540/349 |

FOREIGN PATENT DOCUMENTS

| | | |
|---|---|---|
| 0 277 008 | 1/1988 | European Pat. Off. . |
| 312813 | 4/1989 | European Pat. Off. . |
| 0 387 178 | 2/1990 | European Pat. Off. . |
| 0 594 099 A1 | 10/1993 | European Pat. Off. . |
| 2003863 | 3/1979 | United Kingdom . |
| 2 287 025 | 9/1995 | United Kingdom . |
| 2298201 | 8/1996 | United Kingdom . |
| WO 95/21173 | 8/1995 | WIPO . |
| 95/34194 | 9/1995 | WIPO . |
| 9523870 | 9/1995 | WIPO . |
| 96/33197 | 4/1996 | WIPO . |
| WO 96/28452 | 9/1996 | WIPO . |
| 9705142 | 2/1997 | WIPO . |
| 9708175 | 3/1997 | WIPO . |
| 9747301 | 12/1997 | WIPO . |
| 9821212 | 5/1998 | WIPO . |

OTHER PUBLICATIONS

Abstract of US 4,560,552 (counterpart to GB 1508977), 1985.
Chem. Abstr., vol. 99:37107, 1996.
Chem. Abstr., vol. 87:6692 (1996).
Abstract of JP 55162993 (CA vol. 94:137803), 1996.
Abstract of US 4,110,165 (counterpart to GB 1508977), 1996.
Abstract of US 4,556,559 (counterpart to GB 1508977), 1985.

*Primary Examiner*—Mark L. Berch
*Attorney, Agent, or Firm*—Lydia T. McNally; Stephen G. Kalinchak; George R. Dohmann

[57] ABSTRACT

Process for the production of alkali salts of clavulanic acid of formula

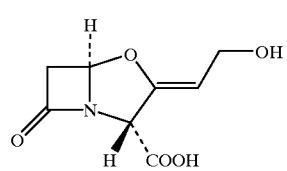

I by conversion of clavulanic acid into a pharmaceutically acceptable salt of clavulanic acid which is characterised in that the conversion is carried out in n-butanol or iso-butanol (2-methyl-1-propanol) as a solvent; and a potassium salt of clavulanic acid containing n-butanol or iso-butanol.

17 Claims, No Drawings

PRODUCTION OF A SALT OF CLAVULANIC ACID

This application is a 371 of PCT/EP96/05015, filed Nov. 14, 1996.

The present invention relates to the production of pharmaceutically acceptable salts of clavulanic acid of formula

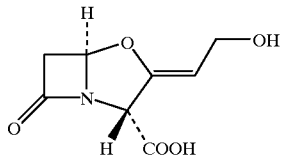

I

Pharmaceutically acceptable salts of clavulanic acid are known and various production processes, for example via
a) fermentation of a micro-organism which is capable to produce clavulanic acid
b) isolation of clavulanic acid from the fermentation broth
c) purification of clavulanic acid, e.g. via a salt thereof
d) conversion of the purified clavulanic acid of step c), e.g. of a salt thereof into a pharmaceutically acceptable salt of clavulanic acid
are disclosed.

Fermentation step a) may be carried out, for example, as generally described e.g. in GB 1508977 and WO 93/25557. A particular fermentation process, is disclosed, e.g. in EP 182 522 by continuously or intermittently feeding a carbon source during fermentation; e.g. in WO 96/18743 by keeping low levels of ammonium and urea; e.g. in EP 349 121; WO 95/03416; CA 2108113; WO 94/18326; WO 94/12654; and WO 96/10084; by production of clavulanic acid from a host transformed with a vector comprising a DNA or a DNA fragment that is encoding at least one enzyme involved in clavulanic acid production. An appropriate micro-organism may be for example a micro-organism of the genus Streptomyces, such as S. clavuligerus, i.e. strain NRRL 3585, or Streptomyces sp. P6621 FERM 2804 (Japanese patent 55,162,993) or other mutants.

Fermentation under appropriate conditions is in more detail known from various publications, e.g. from references cited under step a), the content of which, including prior art citations therein, is incorporated herein by reference.

Isolation step b) may be carried out, for example, by extraction of the acidified fermentation broth with a water-immiscible solvent in which clavulanic acid is soluble, e.g. by direct extraction of the fermentation broth, or after removing at least part of the suspended solids suspended in the fermentation broth. Solids may be removed, for example by flocculation, filtration, e.g. by microfiltration, or by centrifugation. A water-miscible solvent may be added to the fermentation broth in order to improve filterability of the broth prior to solid removal. The aqueous, clavulanic acid containing liquid may be pre-concentrated, conveniently prior to acidification and extraction, to achieve specific concentration ranges, e.g. by anion exchange or osmotic methods. The solution of clavulanic acid in an organic solvent, for example obtainable by extraction, may be e.g. back-extracted into water for further purification. Phase separation of the aqueous and the organic phase may be facilitated, for example by centrifugation methods. The solution of clavulanic acid in an organic solvent may be dried to achieve specific water ranges prior to further processing. Isolation processes using appropriate conditions are in more detail known from various publications, e.g. from EP 387 178; WO 93/25557; WO 95/11295; WO 95/34194: WO 96/28452; WO 96/22296. The content of references cited under step b), including prior art citations therein, is incorporated herein by reference.

Purification step c) may for example be carried out by chromatography or via salt formation, for example via formation of a salt of clavulanic acid that may precipitate, for example crystallise, from the solvent used. Such a salt may be, for example the lithium salt of clavulanic acid, e.g. as described in GB 1543563, or GB 1508977, or an amine salt. Suitable amines which form a salt with clavulanic acid are described in various publications, such as tert.butylamine in EP 26 044; N,N-(di)alkyl-alkylene-diamines, such as diisopropyl-ethylendiamine in EP 562 583; N,N,N',N'-tetramethyl-ethylendiamine in EP 719 778; tert.octylamine for example in GB 2264944; or for example a class of amines in WO 93/25557, wherein are described amines of formula

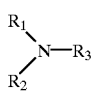

II wherein $R_1$, $R_2$ and $R_3$ are selected according to the following options:
ca) $R_1$ being an optionally substituted cyclic group of general formula

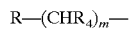

wherein
m is zero or an integer 1 to 5
R is an optionally substituted aliphatic hydrocarbon ring system containing from 3 to 8 ring carbon atoms
$R_4$ is hydrogen or alkyl, amino- or hydroxy substituted alkyl; or substituted amino-substituted alkyl; or a group of the same general formula $R_1$ above;
$R_2$ and $R_3$ are independently selected from the same groups from which $R_1$ is selected; or from hydrogen; alkyl; alkenyl; amino- or hydroxy-substituted alkyl or alkenyl; or substituted amino-substituted alkyl or alkenyl;
or
cb) $R_1$, $R_2$ and $R_3$ are the same or different and are independently selected from hydrogen; alkyl; alkenyl; amino- or hydroxy- or alkoxy-substituted alkyl or alkenyl; or substituted amino-substituted alkyl or alkenyl; or
cc) $R_1$ being an optionally substituted aryl group of general formula

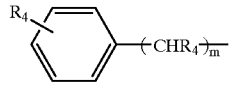

wherein
$R_4$ is hydrogen or one or more substituents, and m is zero or an integer of 1 to 5, $R_2$ and $R_3$ are independently selected from hydrogen; alkyl; amino- or hydroxy-substituted alkyl; or substituted amino-substituted alkyl; or groups of the same general formula from which $R_1$ is selected; or
cd) $R_1$ and $R_2$ and optionally $R_3$ together with the nitrogen atom shown being the residue of an optionally substituted heterocyclic ring system including the nitrogen atom as a ring member, and optionally including one or more additional ring hetero atoms: and, if $R_3$ is not part of the ring system $R_3$ is independently selected from hydrogen, alkyl, amino- or hydroxy-substituted alkyl or substituted amino-substituted alkyl; or ce) $R_1$ being a group of general formula

wherein
$R_4$ and $R_5$ are independently hydrogen; alkyl; amino-substituted alkyl; or substituted amino-substituted alkyl; and
$R_2$ and $R_3$ are independently selected from hydrogen; alkyl amino- or hydroxy substituted alkyl; or substituted amino-substituted alkyl; and
m is zero or an integer of 1 to 5; or cf) one or both of $R_1$ and $R_2$ are hydrogen and
$R_3$ represents the residue of an amino acid in which the carboxylate group of the amino acid may be esterified or in the form of an amine.

The amine may e.g. further be as described in WO 94/22873, such as an amine of formula

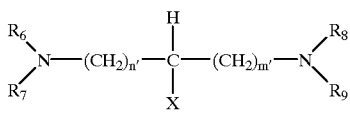

wherein
$R_6$ and $R_7$ are each $C_{1-8}$alkyl; $C_{3-8}$cycloalkyl; or $C_{3-8}$cycloalkyl-$C_{1-8}$alkyl; optionally substituted by one or more inert substituents; or are interlinked to form a ring of 4 to 7 ring atoms,
$R_8$ and $R_9$ are each $C_{1-8}$alkyl; $C_{3-8}$cycloalkyl; or $C_{3-8}$cycloalkyl-$C_{1-8}$alkyl; optionally substituted by one or more inert substituents; or are interlinked to form a ring of 4 to 7 ring atoms,
X is hydrogen or a hydrogen bridge forming group, and
m' and n' independently denotes an integer of zero to 5.
Specifically mentioned are the amines N,N,N',N'-tetramethyl-1,2-diaminoethane and 1,3-bis(dimethylamino)-2-propanol.

The amine may e.g. further be as described in WO 96/20199, such as an amine of formula

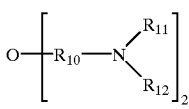

wherein $R_{10}$ is an alkylene group, optionally substituted by one or more inert substituents; and
$R_{11}$ and $R_{12}$ denote independently hydrogen or alkyl, optionally substituted by one or more inert substituents; or
$R_{11}$ and $R_{12}$ together with the nitrogen atom form a heterocyclic ring having 4 to 7 carbon atoms, optionally substituted by one or more inert substituents.

The amine may e.g. further be as described in EP 729 961, such as an amine of formula

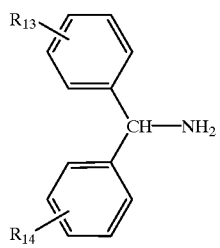

wherein
$R_{13}$ and $R_{14}$ independently represent a hydrogen atom or a pharmaceutically acceptable substituent.

The amine may e.g. further be as described in WO 94/21647, such as an amine of formula

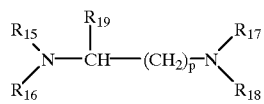

wherein
$R_{15}$, $R_{16}$, $R_{17}$, and $R_{18}$ denotes a hydrogen atom; a straight chain or a branched chain $C_{1-8}$ alkyl group; an aralkyl group wherein the alkyl group is a methyl or ethyl group and the aryl group is a phenyl group, which is optionally substituted by an N-alkyl or N,N-dialkyl group wherein the alkyl groups are $C_{1-4}$ alkyl; or
$R_{15}$, $R_{16}$, $R_{17}$ and $R_{18}$ jointly independently denotes a cyclic alkylene ring having 3 to 6 methylene groups, one of these groups being optionally substituted by an oxygen or a sulphur atom or by an amino group; and
$R_{19}$ denotes a hydrogen atom or a methyl group; and
p denotes an integer from 1 to 3.

Purification under appropriate conditions is in more detail known from various publications, e.g. from references cited under step c), the content of which, including prior art citations therein, is incorporated herein by reference.

In a process according to point d) clavulanic acid may be converted as such; or in form of a labile derivative thereof, for example a salt thereof, for example a lithium salt or a sodium salt thereof; or in form of an amine salt thereof. For salt formation the amine may be contacted with clavulanic acid in solution, in an organic solvent or solvent system. Conveniently the same solvent may be used which was used for extraction of clavulanic acid from the aqueous phase, for example of the optionally pre-treated fermentation broth. Prior to contacting the clavulanic acid containing organic solution with an amine the solution may be preconcentrated. Contacting clavulanic acid with the amine may be carried out by any appropriate method, for example the amine may be added to a solution of clavulanic acid in an organic solvent, for example by simple addition to the solution of clavulanic acid in a solvent, or, e.g. by mixing an amine into a stream of a solution of clavulanic acid in a solvent. The desired salt of clavulanic acid with an amine may be isolated from the organic solvent, for example by filtration or centrifugation, if the salt forms a solid, for examples if the salt crystallises. A second solvent may be added to the mixture containing clavulanic acid, the solvent and the amine that may cause precipitation of the amine salt of clavulanic acid. The amine salt of clavulanic acid may be obtained in form of a solvate, for example of the acetone solvate. Recrystallisation of the amine salt of clavulanic acid may be effected. If the solvent is wholly or partly immiscible with water, the amine salt of clavulanic acid may also be extracted into water to form an aqueous solution of the salt, which may be very concentrated, as e.g. is described in WO 95/21173. Conditions such as reaction conditions, specific reaction conditions, reagents, amount ranges of reagents, concentration ranges, temperatures, etc. for purification and/or isolation of a salt of clavulanic acid, for example an amine salt, are known from, for example, references cited under points a), b) and c), the content of which, including prior art citations therein, is incorporated herein by reference.

Conversion step d) may be carried out according to known methods. A pharmaceutically acceptable salt of clavulanic acid may be, for example, a salt of clavulanic acid with pharmaceutically acceptable alkali or alkaline earth metals, preferably a potassium salt. Generally, clavulanic acid, or a salt thereof, for example an amine salt thereof, conveniently in solution, is contacted with a cation source which is able to form a pharmaceutically acceptable salt of clavulanic acid. Suitable cation sources are described, for example in references cited above. A preferred cation source may be an alkali or earth alkali salt of a carboxylic acid, for example 2-ethylhexanoic acid, for example the potassium salt thereof, or e.g. an acetate, optionally in combination with acetic acid. Conditions such as reaction conditions, specific reaction conditions, reagents, amount ranges of reagents, concentration ranges, temperatures, etc. for purification and/or isolation of a salt of clavulanic acid, for example an amine salt, are known from, for example, references cited under points a), b) and c), the content of which, including prior art citations therein, is incorporated herein by reference.

In fact, in many of the references cited above conversion of an amine salt of clavulanic acid in a solvent, which is practically ethanol or iso-propanol, by addition of 2-ethylhexanoic acid potassium salt or potassium acetate to give a potassium salt of clavulanic acid which may precipitate, for example crystallise is described. In such a process generally a few percent of water are added and during conversion additional water is formed. Water contaminates the solvents used and thus creates problems in recycling the solvents. Since ethanol and iso-propanol forms azeotropes with water, recycling is difficult and the water is to be removed from the solvent by means of ternary azeotropes, e.g. by addition of optionally substituted benzene, other aromatic hydrocarbons or cyclohexane. Such solvents may, however, contaminate the recycled solvent.

We have now surprisingly found a solvent in which clavulanic acid, for example in form of a salt thereof, for example in form of the amine salt thereof, may be converted in the presence of an appropriate cation source to give a pharmaceutically acceptable salt of clavulanic acid in high yields and purities and which is additionally easily to recover, without using further solvents. These solvents may be used on technical scale.

In one aspect the present invention provides a process for the production of a pharmaceutically acceptable salt of clavulanic acid of formula I by conversion of clavulanic acid into a pharmaceutically acceptable salt of clavulanic acid which is characterised in that the conversion is carried out in n-butanol or iso-butanol (2-methyl-1-propanol) as a solvent. The solvents n-butanol and iso-butanol may be used in mixture, or preferably either n-butanol or iso-butanol is used.

In another aspect the present invention provides the use of n-butanol or of iso-butanol in the production of a pharmaceutically acceptable salt of clavulanic acid of formula I by conversion of clavulanic acid into a pharmaceutically acceptable salt of clavulanic acid.

Clavulanic acid may be converted as such, or in form of a salt thereof, for example a lithium salt or a sodium salt or an amine salt thereof. Preferably an amine salt of clavulanic acid, for example such as disclosed in the references cited above, for example in form of a solvate, such as an acetone solvate may be used. An amine salt as described above in any of the references may be used. Preferred amine salts include salts of clavulanic acid with tert.butylamine, tert.octylamine (2-amino-2,4,4-trimethylpentane), N,N'-diisopropyl-ethylene-diamine, N,N,N',N'-tetramethyl-diaminoethane and 1,3-bis(dimethylamino)-2-propanol, more preferably salts with tert.octylamine or tert.butylamine.

In another aspect the present invention provides a process for the production of a pharmaceutically acceptable salt of clavulanic acid of formula I by conversion of a salt of clavulanic acid, for example an amine salt thereof, for example the amine salt is selected from a salt of clavulanic acid with tert.butylamine, tert.octylamine (2-amino-2,4,4-trimethyl-pentane), N,N'-diisopropyl-ethylene-diamine, N,N,N',N'-tetramethyl-diaminoethane or 1,3-bis (dimethylamino)-2-propanol, into a pharmaceutically acceptable salt of clavulanic acid which is characterised in that the conversion is carried out in n-butanol or iso-butanol as solvent.

A pharmaceutically acceptable salt of clavulanic acid may be a pharmaceutically acceptable alkali or earth alkali salt of clavulanic acid, for example a potassium salt.

In another aspect the present invention provides a process for the production of a potassium salt of clavulanic acid of formula I by conversion of clavulanic acid, for example in form of a salt, for example in form of an amine salt thereof, for example in form of a salt of clavulanic acid with an amine selected from tert.butylamine, tert.octylamine (2-amino-2,4,4-trimethylpentane), N,N'-diisopropyl-ethylene-diamine, N,N,N',N'-tetramethyl-diaminoethane or 1,3-bis(dimethylamino)-2-propanol, into a potassium salt of clavulanic acid which is characterised in that the conversion is carried out in n-butanol or iso-butanol as solvent.

Conversion according to the present invention may be carried out in usual manner, for example as described in any of the references cited above under points a), b), c) and d), the content of which, including prior art citations therein, is incorporated herein by reference, using, however, n-butanol or iso-butanol as solvent, and may be preferably carried out as follows:

Clavulanic acid, e.g. a salt thereof, preferably an amine salt thereof may be dissolved in n-butanol or iso-butanol. Water may be present. A low amount of water may be used, such as 0.5 to 10%, e.g. 1.0 to 5%, for example 1.0 to 4%, for example 1.5 to 3.0%. The amount of n-butanol or iso-butanol in respect to clavulanic acid is not critical; it should be sufficient to ensure dissolution of the salt, optionally in the presence of water. For example, if a clavulanic amine salt is used, the amount may be dependent on the nature of the amine used for formation of the amine salt. Per g of the amine salt of clavulanic acid 3 ml to 15 ml, for example 4 ml to 12 ml of n-butanol or iso-butanol may be used. Dissolution may be supported by warming the solvent system up to about 45° C., for example 35° C. The solution may be treated with activated carbon to remove, for example coloured by-products and filtrated, optionally prior to further treatment, to obtain a clear solution. The solution of clavulanic acid may be contacted with a cation source which is able to form a pharmaceutically acceptable salt of clavulanic acid. A cation source may be any appropriate carbon source, for example as described in any of the references cited above, the content of which, including prior art citations therein, is incorporated herein by reference, for example a pharmaceutically acceptable alkali or earth alkali salt and may be preferably a salt of a $C_{2-8}$carboxylic acid, more preferably a salt of 2-ethyl-hexanoic acid, for example the potassium salt thereof or a pharmaceutically acceptable acetate, for example a potassium acetate. An acetate may be used optionally in combination with acetic acid. If acetic acid is used in combination with an acetate, per equivalent of the acetate about 1 to 5 mol, for example about 1.5 to about 3 mol, such as 1.5 to about 2.5 mol of acetic acid may be used. The contact of the cation source with clavulanic acid may be carried out as conventional, for example as described in any of the references above, the content of which, including prior art citations therein, is incorporated herein by reference; for example a solution of the cation source, preferably in the same solvent as used for dissolution of clavulanic acid may be added to the solution of clavulanic acid. The amount of the solvent, for example n-butanol or iso-butanol is not critical; it should be sufficient to dissolve the cation source used and may be, for example dependent on the chemical nature of the cation source and the amount of other substances added, such as water, or if the cation source is an acetate, such as acetic acid. If, for example a salt of carboxylic acid is used, such as potassium 2-ethyl-hexanoate as cation source, per mmol of the salt about 0.2 ml and more, such as 0.5 ml and more may be used. If an acetate, for example potassium acetate is used, per g of potassium acetate, for example 1.5 ml and more, for example 2.0 ml and more, such as about 2.0 ml to about 2.5, optionally in the presence of acetic acid, may be used. If acetic acid is used in combination with an acetate, acetic acid may be present either in the clavulanic acid solution, or in the acetate solution. The cation source may be added at once, or in several portions. Addition temperature is not critical and may be, e.g. according to any of the references cited above, the content of which, including prior art citations therein, is incorporated herein by reference, conveniently below 0° C. to about room temperature, for example from about 0° C. to about 25° C., such as from about 10° C. to about 20° C. Ranges of the cation source used in respect to clavulanic acid may be used, for example as described in any of the references cited above, the content of which, including prior art citations therein, is incorporated herein by reference, e.g. one mol of the clavulanic acid (salt) may be contacted with at least one equivalent of the cation source, for example a pharmaceutically acceptable alkali salt or earth alkali salt, such as a potassium salt. The cation source may be added in an excess in respect to clavulanic acid. Preferably per mol of clavulanic acid about 1.0 to about 3.0 equivalents, more preferably about 1.1 to 2.0 equivalents of the cation source may be added. On contact of the clavulanic acid with the cation source a pharmaceutically acceptable salt of clavulanic acid may precipitate, for example crystallise. A second solvent causing precipitation may be added, if desired, as described in any of the references cited above, the content of which, including prior art citations therein, is incorporated herein by reference. Prior to isolation of the pharmaceutically acceptable salt of clavulanic acid the reaction mixture may be stirred for some time and cooled to temperatures as, for example described in any of the references cited, e.g. from less than 0° C. to about 10° C., for example from about 0° C. to about 5° C., in order to obtain complete conversion. The pharmaceutically acceptable salt is isolated, for example in conventional manner, for example as described in any of the references cited above, preferably by filtration or centrifugation, more preferably by filtration, optionally washed with an organic solvent wherein the salt is insoluble or only soluble to a slight excess, as, for example described in any of the references cited above, for example acetone and dried.

A crystalline potassium salt of clavulanic acid may be obtained in rosette free form, for example according to the present examples; or in form of rosettes, as described, for example in EP 277008. the content of which is incorporated herein by reference, including references cited therein.

A pharmaceutically acceptable salt of clavulanic acid, for example the potassium salt of clavulanic acid, containing as a trace component n-butanol or iso-butanol, for example up to 5% per weight or less; 4% per weight or less; 3% per weight or less; 2% per weight or less; and 1% per weight or less; such as up to about 0.6% per weight or less, e.g. 0.5% per weight or less, e.g. from 0.1% per weight or less to 0.6% per weight, e.g. 0.1% per weight to 0.6% per weight is new and forms also part of the present invention. Such formulations are pharmaceutically acceptable and well tolerated.

In another aspect the present invention provides a pharmaceutically acceptable salt of clavulanic acid containing as a trace component n-butanol or iso-butanol, for example up to 5% per weight or less, such as up to 0.6% per weight or less.

An amine salt of clavulanic acid may be obtained by contacting an amine with an impure solution of clavulanic acid in an organic solvent, for example as described above, or as described in any reference cited herein, including references cited therein. An impure solution of clavulanic acid in an organic solvent may be obtained by extraction of an impure acidified aqueous solution of clavulanic acid with an organic solvent, for example as described above, or as described in any reference cited herein, including references cited therein. An impure acidified aqueous solution of clavulanic acid may be obtained from a fermentation broth which is acidified after fermentation has terminated, and/or from a fermentation broth which is harvested partially during fermentation and acidified, for example as described above, or as described in any reference cited herein, including references cited therein. The impure aqueous solution of clavulanic acid may be pre-concentrated prior to acidification, for example as described above, or as described in any reference cited herein, including references cited therein. The fermentation broth may be directly extracted with an organic solvent or at least parts of the solids suspended in the fermentation broth may be removed prior to extraction with an organic solvent, and optionally prior to acidification, for example as described above, or as described in any reference cited herein, including references cited therein. A fermentation broth containing clavulanic acid may be obtained from fermentation of a microorganism which is capable to produce clavulanic acid, for example as described above, or as described in any reference cited herein, including references cited therein.

In another aspect the present invention provides a process for the production of a pharmaceutically acceptable salt of clavulanic acid of formula I by conversion of clavulanic acid, for example in form of an amine salt, into a pharmaceutically acceptable salt of clavulanic acid, wherein the amine salt is obtained by contacting an amine with an impure solution of clavulanic acid in an organic solvent, and, if desired, is isolated, wherein an impure solution of clavulanic acid in an organic solvent is obtained by extraction of an impure acidified aqueous solution of clavulanic acid with an organic solvent, wherein an impure acidified aqueous solution of clavulanic acid is obtained from a fermentation broth which is acidified after fermentation has terminated, and/or from a fermentation broth which is harvested partially during fermentation and acidified, wherein the impure aqueous solution of clavulanic acid is pre-concentrated, if desired prior to acidification wherein the fermentation broth is either directly extracted with an organic solvent, or wherein at least parts of the solids suspended in the fermentation broth are removed prior to extraction with an organic solvent, wherein the fermentation broth containing clavulanic acid is obtained from fermentation of a micro-organism which is capable of producing clavulanic acid.

In another aspect the present invention provides a process for the production of an alkali salt of clavulanic acid of formula

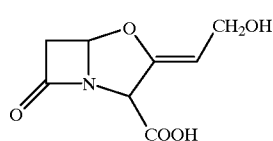

$I_p$ from an amine salt of clavulanic acid by addition of an alkali salt, characterised in that iso-butanol or n-butanol is used as the solvent.

The solvents according to the present invention, i.e. n-butanol and iso-butanol have the advantage that the polarity is surprisingly sufficiently high to dissolve amine salts of clavulanic acid the polarity is surprisingly sufficiently low that the alkali salts remain practically undissolved they may be recovered in dry form by simple hetero azeotropic rectification without the addition of a further solvent to form a hetero-azeotrope.

The potassium salt of clavulanic acid obtained according to the process of the present invention is useful as an antibiotic and particular useful, for example in mixture with another antibiotic such as, for example amoxicillin, e.g. amoxicillin trihydrate. Such a mixture may have specific characteristics, as described for example in GB 2005538 and WO 95/28927. A mixture of potassium clavulanate containing n-butanol or iso-butanol with amoxicillin, for example useful in a composition for administration, is new. A mixture of potassium clavulanate containing n-butanol or iso-butanol with amoxicillin, e.g. amoxicillin trihydrate, for example in ranges as described in GB 2005538 and WO 95/28927 is new and also forms part of the present invention.

In another aspect the present invention provides a mixture containing a potassium salt of clavulanic acid which contains n-butanol or iso-butanol and amoxicillin.

Mixtures of a potassium salt of clavulanic acid and amoxicillin in specific ranges, including a pharmaceutically acceptable carrier and/or diluent may be prepared, for example as described in GB 2005538 and WO 95/28927. the content thereof is incorporated herein by reference, including prior art citations therein.

The solvents used in the conversion of clavulanic acid, for example of a salt of clavulanic acid, such as an amine salt of clavulanic acid, i.e. n-butanol or iso-butanol may be recovered easily, although the solvents contain water added optionally in the conversion step and/or formed during conversion. This may be carried out, for example by use of a hetero-azeotropic rectification column system having a device for separating off azeotropic mixtures, such as a so called azeotropic head. Practically water-free n-butanol or iso-butanol and water which is practically free of n-butanol or iso-butanol may be obtained using for example a rectification system as described in Example A below.

In another aspect the present invention provides a process wherein n-butanol or iso-butanol used in the conversion of clavulanic acid into a pharmaceutically salt of clavulanic acid is recovered by azeotropic distillation to obtain practically water-free n-butanol or practically water-free iso-butanol; and water which is practically free from n-butanol or iso-butanol.

Any reference cited herein, including references cited therein, is incorporated herein by reference in any aspect of the present invention.

In the following examples all temperatures are given in degrees Celsius. The content of n-butanol or iso-butanol in the potassium clavulanate obtained according to the examples is from about 0.2% to about 0.6% per weight.

EXAMPLE 1

4.5 g of 2-amino-2,4,4-trimethylpentane-(2R,5R,Z)-3-(2-hydroxyethylidene)-7-oxo-4-oxa-1-azabicyclo[3,2,0]-heptane-2-carboxylate (tert.octylamine salt of clavulanic acid) are dissolved in 50 ml of 2-methyl-1-propanol, containing 2.5% water. 0.22g of activated carbon (Norite CG1) are added under stirring within ca. 30 minutes and the mixture is clear-filtered. At 10°, over the course of ca. 25 minutes under vigorous stirring, 10 ml of a 2-molar solution of 2-ethyl-hexanoic acid potassium-salt in 2-methyl-1-propanol is added. The mixture is cooled to +4° and stirred for ca. 2 hours. A precipitate is formed which is filtrated off, washed with 50 ml of acetone and dried for 18 hours at 20° and at 1 mbar. Potassium clavulanate is obtained (confirmed by $^1$H-NMR).

EXAMPLE 2

10 g of 2-amino-2,4,4-trimethylpentane-(2R,5R,Z)-3-(2-hydroxyethylidene)-7-oxo-4-oxa-1-azabicyclo[3,2,0]-heptane-2-carboxylate (tert.octylamine salt of clavulanic acid) are dissolved in 100 g of 2-methyl-1-propanol, containing 2.5% water, and clear-filtered. At 20°, within ca 30 minutes under vigorous stirring, 20 ml of a 2-molar solution of 2-ethyl-hexanoic acid potassium salt in 2-methyl-1-propanol are added. The mixture is cooled to +4° and crystallisation is allowed to complete within about 2 hours. A precipitate is formed which is filtrated off, washed with 100 ml of acetone and dried for 16 hours at 20° and at 1 mbar. Potassium clavulanate is obtained (confirmed by $^1$H-NMR).

EXAMPLE 3

10.0 g of tert.butylamine-(2R,5R,Z)-3-(2-hydroxyethylidene)-7-oxo-4-oxa-1-azabicyclo[3,2,0]-heptane-2-carboxylate (tert.butylamine salt of clavulanic acid) are dissolved in 40 ml of 2-methyl-1-propanol, containing 2% water, and clear-filtered. At 20°, within ca. 15 minutes under vigorous stirring, 20.2 ml of a 2-molar solution of 2-ethyl-hexanoic acid potassium-salt in 2-methyl-1-propanol are added. The mixture is cooled to +4° and stirred for ca. 2 hours. A precipitate is formed which is filtrated off, washed with 50 ml of acetone and dried for about 15 hours at 20° and at 1 mbar. Potassium clavulanate is obtained (confirmed by $^1$H-NMR).

EXAMPLE 4

13.6 g of tert.octylamine salt of clavulanic acid are dissolved in 170 g of n-butanol, containing 5.0% water. 0.4 g of activated carbon (Norite CG-1) are added. After ca. 30 minutes, the mixture is clear-filtered. At 100, within ca. 30 minutes under vigorous stirring, 40 ml of a 2-molar solution of 2-ethyl-hexanoic acid potassium salt in n-butanol are added. The mixture is cooled to +4° and stirred for ca. 2 hours. A precipitate is formed which is filtrated off, washed with 50 ml of acetone and dried for 18 hours at 22° and at 1 mbar. Potassium clavulanate is obtained (confirmed by $^1$H-NMR).

EXAMPLE 5

5.5 g of tert.octylamine salt of clavulanic acid are dissolved in 60 ml of iso-butanol, containing 3.0% of water at a temperature of about 35°. 0.32 g of active carbon (Norit CG 1) are added. The suspension is stirred for ca. 15 minutes, filtrated and the filtrate is washed with 20 ml of iso-butanol. The solution is cooled to about 15° and 0.2 ml of acetic acid are added. 2.1 g of potassium acetate are dissolved in 55 ml of iso-butanol, containing 0.25 ml of water and added slowly to the reaction mixture. The mixture is cooled to ca. 2° and stirred for ca. one hour. A precipitate is formed which is filtrated off, washed with 30 ml of acetone and dried for about 20 hours in vacuo at ca. 45°. Potassium clavulanate is obtained.

$^1$H-NMR (300 Mhz in $D_2O$ against 3-trimethylsilyl propionic acid-$d_4$-Na): 3.14 (1H, d, J=17.0 Hz, H-6), 3.57 (1H. dd, J=17.0 and 2.8 ppm, H-6'), 4.19 (2H, d, J=7.4 Hz, $CH_2$—OH), 4.91–4.96 (2H, m, H-2 and =CH), 5.73 (1H, d, J=2.8 Hz, H-5).

EXAMPLE 6

5.5 g of the tert.octylamine salt of clavulanic acid are dissolved in 55 ml of iso-butanol, containing 3.0% of water, at a temperature of about 35°. 0.32 g of active carbon (Norit CG 1) are added. The suspension is stirred for ca. 15 minutes, filtrated and the filtrate is washed with 20 ml of iso-butanol. The mother liquor solution is cooled to about 10°. 2.1 g of potassium acetate are dissolved in 55 ml of iso-butanol, containing 0.25 ml of water and 0.3 ml of acetic acid, and added slowly to the reaction mixture. The mixture is cooled to ca. 5° and stirred for ca. 2 hours. A precipitate is formed which is filtrated off, washed with 30 ml of acetone and dried for about 20 hours in vacuo at ca. 45°. Potassium clavulanate is obtained (confirmed by $^1$H-NMR).

EXAMPLE 7

5.5 g of the tert.octylamine salt of clavulanic acid are dissolved in 50 ml of butanol containing 3.0% of water. 0.32 g of active carbon (Norit CG 1) are added. The suspension is stirred for ca. 15 minutes, filtrated and the filtrate is washed with 20 ml of butanol. The mother liquor solution is cooled to about 10°. 2.1 g of potassium acetate are dissolved in 50 ml of butanol and this solution is added slowly to the reaction mixture. The mixture is cooled to ca. 4° and stirred for ca. 2 hours. A precipitate is formed which is filtrated off, washed with 30 ml of acetone and dried for about 20 hours in vacuo at ca. 40°. Potassium clavulanate is obtained (confirmed by $^1$H-NMR).

EXAMPLE 8

5.5 g of the tert.octylamine salt of clavulanic acid are dissolved in 50 ml of butanol containing 3.0% of water. 0.32 g of active carbon (Norit CG 1) are added. The suspension is stirred for ca. 15 minutes, filtrated and the filtrate is washed with 20 ml of butanol. The solution is cooled to about 10°. 0.3 ml of acetic acid are added. 2.1 g of potassium acetate are dissolved in 50 ml of butanol and the solution is added slowly under vigorous stirring to the reaction mixture. The mixture is cooled to ca. 5° and stirred for ca. 2 hours. A precipitate is formed which is filtrated off, washed with 30 ml of acetone and dried for about 20 hours in vacuo at ca. 45°. Potassium clavulanate is obtained (confirmed by $^1$H-NMR).

EXAMPLE 9

5.5 g of the tert.octylamine salt of clavulanic acid are dissolved in 55 ml of iso-butanol containing 3.0% of water at a temperature of about 35°. 2.1 g of potassium acetate are dissolved in 55 ml of iso-butanol containing 0.25 ml of water and 0.2 ml of acetic acid. 6.0 ml of the potassium acetate solution are added dropwise to the solution of the clavulanic acid. 0.32 g of active carbon (Norit CG 1) are added. The suspension is stirred for ca. 15 minutes, filtrated and the filter is washed with 20 ml of iso-butanol. The solution is cooled to ca. 10° and the remaining solution of potassium acetate prepared as described above is added slowly. The mixture is cooled to ca. 5° and stirred for ca. 2 hours. A precipitate is formed which is filtrated off, washed with 30 ml of acetone and dried for about 20 hours in vacuo at ca. 45°. Potassium clavulanate is obtained (confirmed by $^1$H-NMR).

A potassium salt of clavulanic acid may be obtained in n-butanol or iso-butanol, in anologous manner as described in examples 1 to 9 also, by use of a salt of clavulanic acid with an amine selected from
N,N'-diisopropyl-ethylene-diamine
N,N,N',N'-tetramethyl-diaminoethane
1,3-bis(dimethylamino)-2-propanol
instead of tert.octylamine (2-amino-2,4,4-trimethylpentane) or tert.butylamine.

Example A
Solvent recovery a) 130 ml of primary mother liquor obtained according to example 9 are evaporated in vacuo. The distillate, consisting of iso-butanol containing ca. 1.5–2% water is distilled under normal pressure via a rectification column having an azeotropic head in such a way that the aqueous lower phase which separates off in the azeotropic head (containing about 91% of water) is removed; and the upper phase. containing about 15% of water is fed back into the rectification apparatus. Iso-butanol in the residue in the rectification apparatus becomes water-free when no further lower phase is formed in the azeotropic head. b) The lower aqueous phase in the azeotropic head (containing about 9% iso-butanol) which is removed in step a) may be enriched on iso-butanol in an azeotropic head via a second rectification column by distillation until the hetero-azeotrope composition of water and iso-butanol (=composition before phase separation occurs: about 70% iso-butanol, 30% water) is achieved. The upper phase obtained in the azeotropic head (containing about 85% iso-butanol and water) is removed and the lower phase is fed back into the rectification apparatus. In the residue of the rectification apparatus water which is practically free of iso-butanol is obtained. The upper phase obtained in the azeotropic head may undergo a second rectification as described. An anologous method as described may also be used for separation of water and n-butanol. In this way iso-butanol or n-butanol, practically free of water; and water, practically free of iso-butanol or n-butanol; may be obtained.

I claim:

1. A process for the production of clavulanic acid of the formula

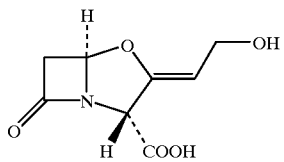

in the form of a pharmaceutically acceptable salt, comprising contacting clavulanic acid or a salt of clavulanic acid with a cation source which is able to form a pharmaceutically acceptable salt of clavulanic acid, characterized in that the reaction is carried out in iso-butanol (2-methyl-1-propanol) as a solvent, and the solvent contains 0.5 to 10% water and wherein the salt of clavulanic acid is different from the clavulanic acid of formula I in the form of a pharmaceutically acceptable salt.

2. A process according to claim 1, wherein clavulanic acid in form of a salt is reacted.

3. A process according to claim 2, wherein clavulanic acid in form of an amine salt is reacted.

4. A process according to claim 3, wherein the amine salt is selected from a salt of clavulanic acid with tert.butylamine, tert.octylamine (2-amino-2,4,4-trimethylpentane), N,N'-diisopropyl-ethylene-diamine, N,N,N',N'-tetramethyl-diaminoethane or 1,3-bis(dimethylamino)-2-propanol.

5. A process according to claim 1, wherein a potassium salt of clavulanic acid is produced.

6. A process according to claim 3, wherein the amine salt is obtained by contacting an amine with an impure solution of clavulanic acid in an organic solvent, and, if desired, is isolated.

7. A process according to claim 6, wherein an impure solution of clavulanic acid in an organic solvent is obtained by extraction of an impure acidified aqueous solution of clavulanic acid with an organic solvent.

8. A process according to claim 7, wherein an impure acidified aqueous solution of clavulanic acid is obtained from a fermentation broth which is acidified after fermentation has terminated, and/or from a fermentation broth which is harvested partially during fermentation and acidified.

9. A process according to claim 8, wherein the impure aqueous solution of clavulanic acid is pre-concentrated prior to acidification.

10. A process according to claim 8, wherein the fermentation broth is directly extracted with an organic solvent.

11. A process according to claim 8, wherein at least parts of the solids suspended in the fermentation broth are removed prior to extraction with an organic solvent.

12. A process for the production of clavulanic acid of the formula

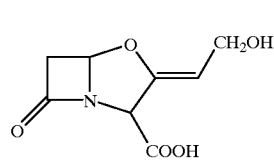

in the form of an alkali salt, wherein the process comprises adding an alkali salt of carboxylic acid to an amine salt of clavulanic acid wherein iso-butanol is used as the solvent and the solvent contains 0.5 to 10% water.

13. A process according to claim 1 wherein iso-butanol used in the conversion of clavulanic acid into a pharmaceutically acceptable salt of clavulanic acid is recovered by azeotropic distillation to obtain practically water-free iso-butanol; and water which is practically free from iso-butanol.

14. The process according to claim 1, wherein the solvent contains 1 to 5% water.

15. The process according to claim 1, wherein the solvent contains 1.5 to 3.0% water.

16. The process according to claim 2, wherein the solvent contains 1 to 5% water.

17. The process according to claim 2, wherein the solvent contains 1.5 to 3.0% water.

* * * * *